United States Patent [19]

Suckling et al.

[11] Patent Number: 5,063,149
[45] Date of Patent: Nov. 5, 1991

[54] PERFORMING AN ENZYME-CATALYZED REACTION

[75] Inventors: Colin J. Suckling; Peter J. Halling, both of Glasgow; Grant A. Johnston, West Kilbride; Linda Brown, Glasgow, all of Scotland

[73] Assignee: Imperial Chemical Industries PLC, London, England

[21] Appl. No.: 389,596

[22] Filed: Aug. 4, 1989

[30] Foreign Application Priority Data

Aug. 4, 1988 [GB] United Kingdom ................ 8818564
Oct. 14, 1988 [GB] United Kingdom ................ 8824145

[51] Int. Cl.$^5$ .......................... C12Q 1/34; C12Q 1/44; C12Q 1/00; C07D 311/82
[52] U.S. Cl. .......................................... 435/4; 435/18; 435/19; 435/23; 435/39; 435/135
[58] Field of Search .................... 435/4, 18, 19, 23, 39, 435/135

[56] References Cited

U.S. PATENT DOCUMENTS 4,267,273  5/1981  Smith ..................................... 435/44
4,711,245  12/1987  Higgins et al. ......................... 435/25

FOREIGN PATENT DOCUMENTS 1580247  11/1980  United Kingdom .
8706138  10/1987  World Int. Prop. O. .

OTHER PUBLICATIONS

Biotech Data Base 88-09718, Roberts et al. 9996F; Biochem Soc. Trans (1988) 16, 3, 273-74.
Chem. Abs. 85:144976(a), Jul. 5, 1976, Asahi et al, J7677432.
Chem. Abs. 85:144978(c), Jul. 5, 1976, Sasage et al, J7677434.

Primary Examiner—Herbert J. Lilling
Attorney, Agent, or Firm—Cushman, Darby & Cushman

[57] ABSTRACT

A process for performing an enzyme-catalyzed reaction in a reaction mixture comprising two phases, a first aqueous phase containing an enzyme which is not accessible and a second substantially non-aqueous phase containing a non-water miscible solvent wherein a compound derived from fluorescein or a substituted fluorescein is present for the purpose of measuring aqueous pH by monitoring spectroscopic properties. Novel compounds derived from fluorescein or a substituted fluorescein which may be used in the process and a method for producing some of the novel compounds are also claimed.

4 Claims, 1 Drawing Sheet

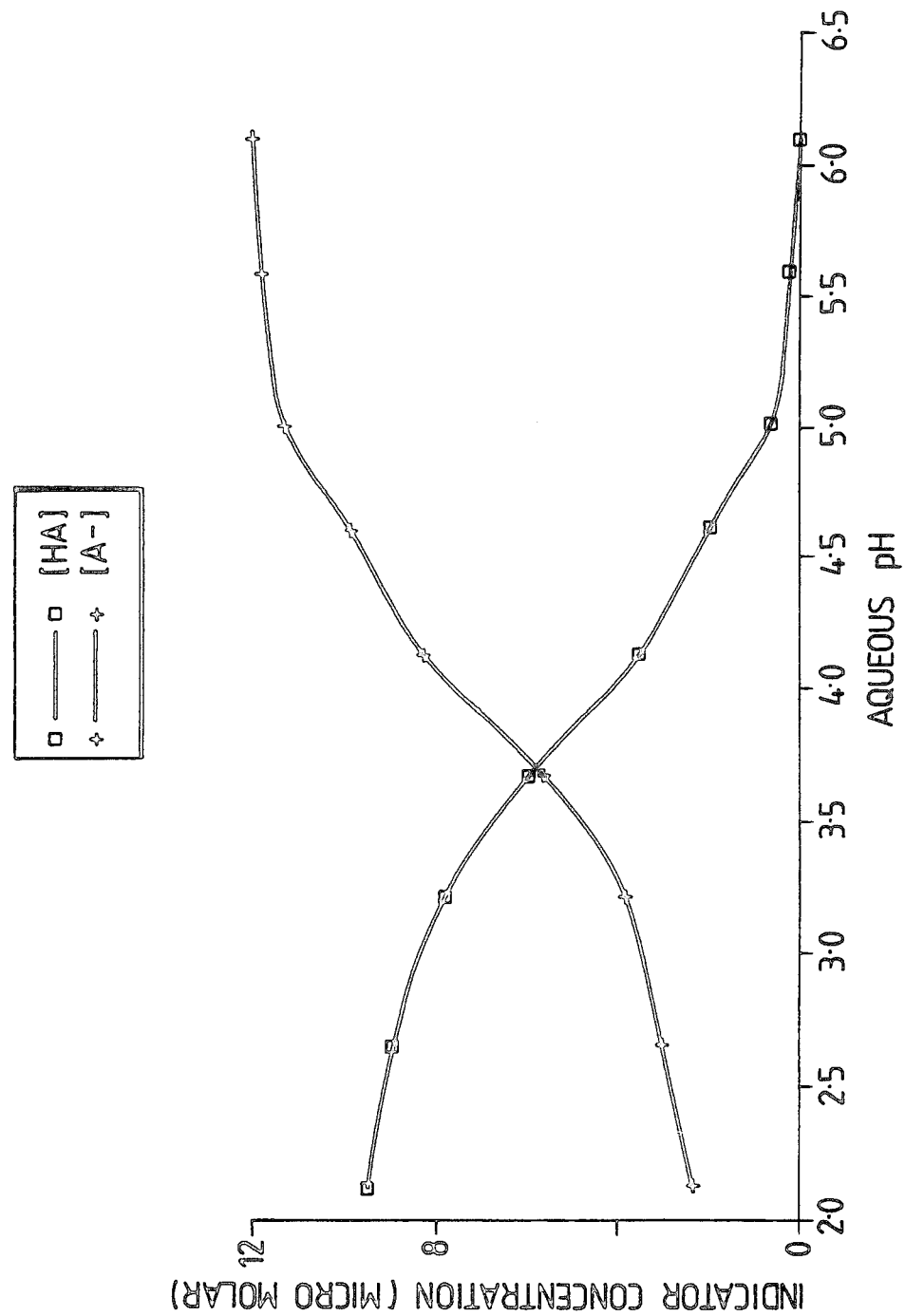

PERFORMING AN ENZYME-CATALYZED REACTION

This invention relates to a process for performing an enzyme-catalysed reaction, to novel compounds for use in the process and to a method for producing the novel compounds.

A large number of enzyme-catalysed reactions are known which involve the use of non-aqueous solvents. Such reactions often rely upon the presence of small amounts of water to allow an aqueous phase to form in the vicinity of enzyme-carrying material. The enzyme-catalysed reaction can then take place in the aqueous phase.

Enzyme-catalysed reactions involving the use of non-aqueous solvents have been known since approximately 1900 but have been little used industrially and have been regarded mainly as curiosities. Increasing numbers of literature reports relating to these reactions have however recently led to industrial interest in them and in the problems associated with them. One problem associated with these reactions is the measurement of pH.

Enzyme catalysed reactions involving the use of non-aqueous solvents often use water immiscible solvents and systems using such water immiscible solvents can be divided into the following three classes:
  A) Systems where there are directly accessible aqueous phases and pH probes can be used;
  B) Systems comprising microemulsions (water droplets of 10 to 10000 molecules) which are transparent and where aqueous phase soluble indicators can be used; and
  C) Systems where aqueous phases are "thermodynamically present" but not accessible.

The systems of interest in connection with the present invention are those of class C). References to such systems include:
  (i) Cambou and Klebanov, Biotechnol. & Bioeng., 26, 1449, (1984)—discusses addition of a water soluble dye; and
  (ii) Cassells and Halling, Biotechnol. & Bioeng., in press—to be published 1989—discusses dilution of the water layer with more water and the use of a pH meter.

We have now prepared a number of novel compounds derived from fluorescein which can be used in the determination of pH during enzyme-catalysed reactions involving the use of non-aqueous solvents by addition to the non-aqueous phase without separating it from the aqueous phase. Previous attempts to produce modified fluorescein-based compounds have generally had the intention of producing water soluble dyes and have therefore produced compounds having different structures from the compounds we have prepared.

According to the present invention we provide a process for performing an enzyme-catalysed reaction in a reaction mixture comprising two phases, a first aqueous phase containing an enzyme which is not accessible and a second substantially non-aqueous phase containing a non-water miscible solvent wherein there is present in the non-aqueous phase a compound having the structural formula (I):

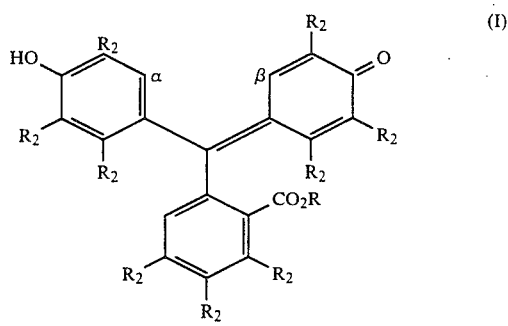

or a compound having the structural formula (II):

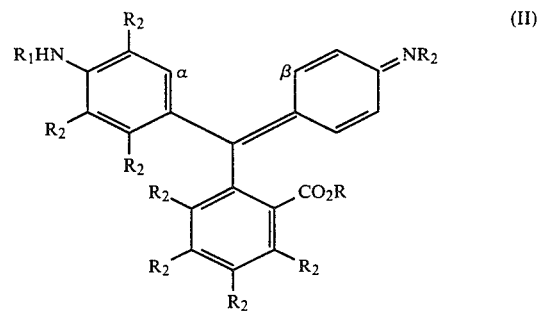

in which positions alpha and beta can be substituted by hydrogen atoms or can be linked together through a bridge comprising 1 or 2 atoms which may have substituents upon them; R is a substituted or unsubstituted hydrocarbon group or a substituted or unsubstituted amide group; $R_1$ is a hydrogen atom, or any other group (the individual groups $R_1$ being the same as or different from each other); and $R_2$ is a hydrogen atom or any other group (individual groups $R_2$ being the same as or different from each other); compound of structural formula (I) or compound of structural formula (II) being present for the purpose of measuring aqueous pH by monitoring spectroscopic properties and calculating the aqueous phase pH therefrom.

Further according to the present invention we provide compounds having the structural formla (III):

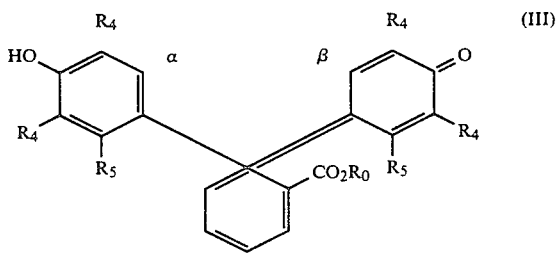

or the structural formula (IV):

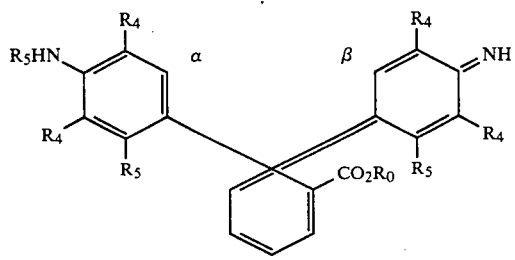

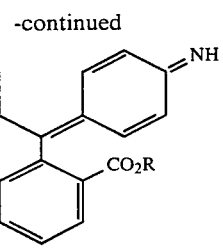

in which positions alpha and beta can be substituted by hydrogen atoms or can be linked together through an oxygen atom; $R_0$ is a substituted or unsubstituted hydrocarbon group (but cannot be methyl or ethyl when $R_4$ and $R_5$ are all hydrogen atoms) or a substituted or unsubstituted amide group; $R_4$ is a hydrogen atom, a halogen atom or an —$NO_2$ group (individual groups $R_4$ being the same as or different from each other); $R_5$ is a hydrogen atom or an alkyl group (individual groups $R_5$ being the same as or different from each other); and $R_5$ is a hydrogen atom, a methyl, ethyl or R group.

Further according to the present invention we provide a method for producing a compound having the structural formula (III)':

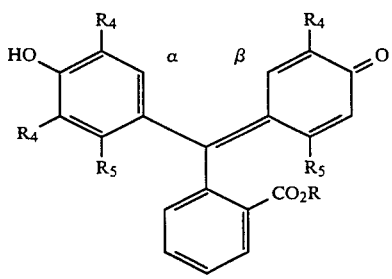

in which positions alpha and beta can be substituted by hydrogen atoms or can be linked together through an oxygen atom; R is a substituted or unsubstituted hydrocarbon group or a substituted or unsubstituted amide group; $R_4$ is a hydrogen atom, a halogen atom or an —$NO_2$ group (individual groups $R_4$ being the same as or different from each other); and $R_5$ is a hydrogen atom or an alkyl group (individual groups $R_5$ being the same as or different from each other) which includes a step wherein fluorescein or a substituted fluorescein is reacted with an alcohol in the presence of sulphuric acid.

In preferred compounds of structural formulae (III) and (IV) the positions alpha and beta are linked together through an oxygen atom and all groups $R_4$ and $R_5$ are hydrogen atoms giving the structures (V) and (VI) respectively:

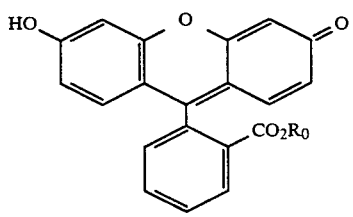

In particularly preferred compounds of structures (III) and (IV), $R_0$ is one of the following groups: isopropyl, octyl, cyclohexyl, phenylethyl, neopentyl (i.e. $(CH_3)_3$—C—$CH_2$—), 3,7-dimethyloctyl or 3,7,11-trimethyldodecyl.

In general in compounds having structural formulae (III) and (IV), when $R_0$ is a hydrocarbon group it may be any hydrocarbon group including alkyl groups both straight and branched, cycloalkyl groups and aromatic groups, unsubstituted hydrocarbon groups being preferred. Preferably when $R_0$ is a hydrocarbon group it is an alkyl group having from 3 to 20 carbon atoms and especially from 8 to 15 carbon atoms. When $R_4$ is a halogen atom it is preferably bromine and when —$NO_2$ groups are used as $R_4$ groups it is preferred that some $R_4$ groups in structural formulae (III) and (IV) are —$NO_2$ groups whilst others are halogen atoms, i.e. the $R_4$ groups in the structures are mixed. When $R_5$ is an alkyl group it is preferably a group having 1 to 5 carbon atoms, particularly 1 to 3 carbon atoms.

In the process of the invention compounds of structural formulae (I) and (II) are preferably compounds of structural formula (III) and (IV). In the process these compounds are usually used in different situations. Thus when the process involves the use of a non-polar acidic molecule compounds of structural formula (I) may be used whilst when the process involves the use of a non-polar basic molecule compounds of structural formula (II) are used. Compounds of either structural formula can be used with neutral reagents. In the presence of a base (proton acceptor), compounds of structural formula (I) are converted from a neutral to an anionic form. In the presence of an acid (proton donor), compounds of structural formula (II) are converted from a neutral to a cationic form. These changes are accompanied by changes in the absorption of light by the compounds in the visible region of the spectrum and can be observed using a spectrophotometer. The different forms have their strongest absorbances in different areas of the visible spectrum. For instance the compound of formula III where $R_0$ is octyl in the neutral form has $\lambda$max=454.9 nm ($\epsilon$15989) whilst in the anionic form $\lambda$max=521 nm ($\epsilon$42683). 2,4,5,7-tetrabromofluorescein, n-octyl ester in the neutral form has $\lambda$max=547 nm ($\epsilon$18432) whilst in the anionic form $\lambda$max=547 nm ($\epsilon$93891). 2,4,5,7-tetrabromofluorescein-3,7.11-trimethyldodecyl ester in the neutral form has $\lambda$max=475.5 nm ($\epsilon$15646) whilst in the anionic form $\lambda$max=545.9 ($\epsilon$79592). Thus if the absorbances at the wavelengths at which the two different forms of formula (I) or formula (II) compound are obtained by calculation from spectrophotometer measurements using the appropriate extraction coefficients, the relative proportions of the two forms can be calculated. This information in turn enables the pH to be determined.

The process of the invention can be used to detect pH changes during enzyme-catalysed reactions involving substantially non-aqueous solvents. Samples of the reaction medium can be taken and used in pH determinations which enable the reaction to be monitored. Any necessary pH changes can then be effected, i.e. if the pH falls outside a pre-determined range buffers can be added to the reaction medium to restore the pH to a value within the range.

Compounds other than those of formulae (III) and (IV) which may be used as compounds of formulae (I) and (II) in the process of the invention include compounds in which the α- and β-positions are connected by bridges containing atoms other than oxygen, e.g. groups such as

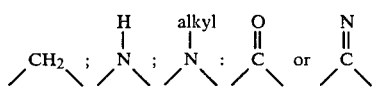

The process of the invention can be used to carry out any enzyme-catalysed reaction involving use of a substantially non-aqueous solvent. An example of such a reaction in which an acidic reagent is used and use of a compound of structural formula (I) is appropriate is the syntheses of esters using lipase enzymes. The process of the invention is very useful for carrying out reactions using solvents such as trichloroethane or diethyl ketone. The proportion of the aqueous phase present during the process of the invention varies depending upon the enzyme, e.g. it can be the amount of water remaining after freeze drying. It can be 200 molecules per molecule of enzyme. In the case of the enzyme chrymotrypsin it can be up to 1 g water per 1 g enzyme.

In addition to their use in the determination of pH during enzyme-catalysed reactions using non-aqueous solvents, the compounds of the invention have other uses. These include the determination of the interfacial area during the mixing of a two-phase system, a property or quality of importance in solvent extraction. During mixing the degree of ionization in the system depends upon the degree of mixing and provides a measure of the extent of mixing.

Any suitable method may be used to prepare the compounds of the invention. A preferred method for the preparation of compounds having the structural formula (I) includes a step in which fluorescein or a substituted fluorecein is reacted with an alcohol in the presence of sulphuric acid. It is preferred that this step is carried out under an inert gas such as nitrogen or argon and at a temperature in the range 100° to 130° C. Preferably the acid is concentrated sulphuric acid. After the step in which the fluorescein reaction with alcohol occurs which produces a product having the basic structure of the compounds of the invention there may be a further step or steps to introduce substituents onto the basic structure, e.g. the product of the basic step may be reacted with bromine to introduce bromine atoms as the $R_1$ groups.

The invention is illustrated by the following Examples:

EXAMPLE 1

Preparation of 3,7,11-Trimethyldodecyl ester of fluorescein

To 3,7,11 trimethyldodecan-1-ol (5 g) was added solid fluorescein (6.5 g). The mixture was stirred at 130° C. under an inert atmosphere for nine hours in the presence of concentrated sulphuric acid (0.5 ml). After cooling, the reaction mixture was dissolved in dilute sodium hydroxide solution. The alkaline solution was thoroughly extracted with ethyl acetate. The ethyl acetate extracts were then washed with dilute sodium hydroxide, dried over anhydrous sodium sulphate and evaporated to yield a red oil (5.3 g).

Analysis of the oil using thin layer chromatography showed product at Rf 0.4 (eluting solvent ethyl acetate) together with unreacted material.

Silica gel column chromatography of oil increasing solvent polarity gradually from 20% ethyl acetate in hexane to 100% ethyl acetate produced unreacted alcohol, unreacted fluorescein and finally crude product ester (1.1 g).

The crude product was purified using preparative thin layer chromatography (silica gel GF$_{254}$) eluting with ethyl acetate.

The pure product ester (Rf 0.4) was extracted from silica using methanol, the methanol being evaporated to give orange-red powder (0.33 g 41%). $^1$H-NMR spectroscopy gave the following result:

$^1$H-NMR 8.07δ 1H double doublet J=7H$_2$, 1H$_7$ H$_A$; 7.64δ 2H multiplet H$_B$; 7.39δ 1H double doublet J=7H$_2$, 1H$_2$ H$_C$; 6.56δ 2H double doublet J=7H$_2$, 1H$_2$ H$_D$; 6.24δ 2H double doublet J=7H$_2$, 1H$_7$ H$_E$; 6.20δ 2H doublet J=1H$_7$, H$_F$; 3.90δ 2H α—CH$_2$— of ester; 1.55δ 1H β—CH$_2$— of ester; 1.10δ 15H ≈ester chain H; 0.81δ 6H doublet J=7H$_7$ "Isopropyl"—CH$_3$; 0.79δ 3H doublet —CH$_3$ J=7H$_3$; 0.71δ 3H doublet J=7H$_2$—CH$_3$.

The structure assigned by $^3$H-NMR was

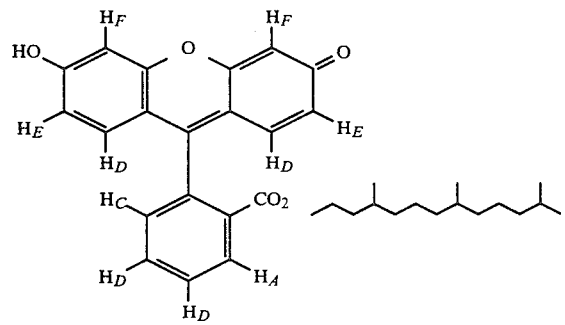

EXAMPLE 2

Preparation of 2,4,5,7-tetrabromofluorescein-3,7,11-trimethyldodecyl ester

Fluorescein 3,7,11-trimethyldodecyl ester (0.05 g) was dissolved in dry methanol and the solution was stirred at room temperature.

To the stirred solution was added bromine (5 equivalents) and the mixture was stirred at room temperature. After 1 hour a red solid precipitate was formed. Stirring was continued for a further hour. The reaction medium was evaporated to dryness, the product taken up in chloroform and filtered and the filtrate analysed by thin layer chromatography (75% ethyl acetate in hexane+1 drop glacial acetic acid as eluent). A chromatogram showed 1 component Rf 0.6.

Product was purified by preparative thin layer chromatography (silica gel GF$_{254}$) using ethyl acetate and a few drops of acetic acid as eluting solvent.

Product was extracted from silica using methanol and the solvent evaporated to give a dark red powder. This powder was taken up in chloroform, the solution filtered and evaporated to dryness to give a red powder. A few mls of hexane were added to the powder and with scratching a crystalline solid was recovered (0.056 g., 71%). ¹H-NMR spectroscopy gave the following result:

²H-NMR 8.12δ 1H double doublet J=7H₇, 1H₇ H_A; 7.71δ 2H multitriplet H_B; 7.49δ 1H double doublet J=7H₇, 1H₂ H_C; 6.91δ 1H s) H_D which; 6.90δ 1H s) is which?; 3.97δ 2H nm α—CH₂—; 1.49δ 2H nm β—CH₂—; 1.10δ 15H nm ester chain H; 0.84δ 6H 2-isopropyl—CH₃; 0.79δ 3H methyl on chain C-3; 0.59δ 3H methyl on chain C-7.

The structure assigned by ¹H-NMR was:

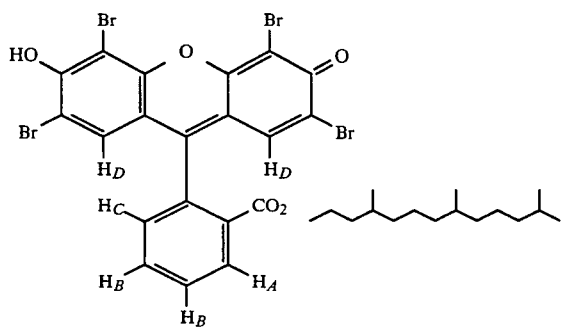

EXAMPLE 3

Preparation of 4,5-Dibromofluorescein-3,7,11-Trimethyldodecyl ester

Fluorescein-3,7,11-trimethyldodecyl ester (0.05 g) was dissolved in dry methanol (5 ml) and the solution was stirred at room temperature. To this solution was added bromine (1 equivalent) and the reaction mixture was stirred at room temperature for 30 minutes.

The reaction mixture was evaporated to dryness, taken up in chloroform and separated using preparative thin layer chromatography (silica gel GF₂₅₄)-eluting with ethyl acetate. Component at Rf 0.3 was extracted using methanol, evaporated to dryness and re-dissolved in hot ethyl acetate. After filtering, the filtrate was evaporated to give a red solid. The solid was scratched in hexane to give a red crystalline solid (0.025 g., 39%).

Structure as 4,5-dibromofluorescein-3,7,11-trimethyldodecyl ester determined ¹H-NMR spectroscopy gave the following result:

¹H-NMR 8.09δ 1H broadened doublet J=7H₇, H_A; 7.76δ 2H multiplet, H_B; 7.41δ 1H broadened doublet J=7H₇, H_C; 6.61δ 1H broadened doublet J=7H₂, 1H_C; H_E; 6.25δ 2H doublet J=7H₇, H_F; 3.94δ 2H multiplet α—CH₂— of ester; 1.50δ 2H multiplet β—CH₂— of ester; 1.10δ 15H multiplet chain hydrogen atoms of ester; 0.85δ 6H doublet J=7H₇ "end-methyls"; 0.79δ 3H doublet J=7H₇) chain methyl; 0.61δ 3H doublet J=7H₇) groups.

The structure assigned by ²H-NMR was

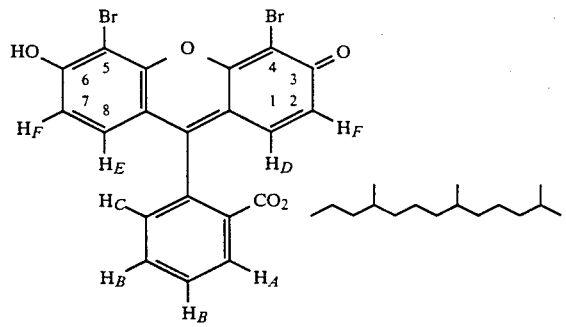

EXAMPLE 4

The method of Example 1 was used to prepare a number of other esters of fluorescein whose relative solubilities in a number of solvents were ascertained. The results are set out in Table 1.

TABLE 1

| Ester of Fluorescein | Relative solubility | | | |
| --- | --- | --- | --- | --- |
| | Water | 0.1 M HCl | 0.1 M NaOH | CH₃CCl₃ |
| 1. Isopropyl- | 3 | 7 | Reacts to give soln of anion | 5.2 |
| 2. Neopentyl- | 1.5 | 1 | Reacts to give soln of anion | 6.3 |
| 3. Cyclohexyl- | 1.3 | Insoluble | Reacts to give soln of anion | 1.0 |
| 4. 2 Phenyl ethyl- | 1 | Insoluble | Reacts to give soln of anion | 2.6 |
| 5. n-Octyl- | Insoluble | Insoluble | Reacts to give soln of anion | 10.9 |
| 6. 3,7,11 Trimethyl | | | | |
| 7. Dodecyl- | Insoluble | Insoluble | Reacts to give soln of anion | 15.0 |

These results show:

(a) The esters become increasingly soluble in water as the size of the ester group is increased;

(b) Solubility in organic solvents increases with size of ester group; and (c) All esters react with sodium hydroxide to give solutions of the sodium salt of anionic form.

Preferred compounds for use in the process of the invention are those with no tendency to enter an aqueous phase when they are already dissolved in an organic solvent and so the above results suggested that 6 and 7 will be most useful in the process of the invention.

EXAMPLE 5

Model Experiment Showing Indicator Response to Aqueous pH Changes

Indicator molecule 2,4,5,7-tetrabromofluorescein-3,7,11-trimethyl dodecyl ester was dissolved in pentan-3-one, forming an orange red solution.

This indicator solution (10 ml) was added to 0.1M aqueous tetra-sodium pyrophosphate buffered solution (10 ml) of known pH in a sealed glass vial.

After shaking vigorously by hand, the organic phase was sampled and analysed using a spectrometer.

This procedure was repeated for a range of values of pH.

Sample results are recorded below in Table 2—the concentrations of each form of the indicator being calculated from the known extinction coefficients of each absorbance.

TABLE 2

| Aqueous pH | $A_{545.9\ n.m.}$ | $A_{475.5\ n.m.}$ | [HA] (μM) | [A] (μM) |
|---|---|---|---|---|
| 6.1 | 0.958 | 0.057 | 0.032 | 12 |
| 5.6 | 0.939 | 0.058 | 0.168 | 11.8 |
| 5.0 | 0.899 | 0.062 | 0.576 | 11.3 |
| 4.6 | 0.787 | 0.076 | 1.9 | 9.86 |
| 4.1 | 0.661 | 0.093 | 3.47 | 8.26 |
| 3.7 | 0.455 | 0.120 | 5.91 | 5.63 |
| 3.2 | 0.320 | 0.140 | 7.81 | 3.79 |
| 2.7 | 0.245 | 0.154 | 8.96 | 2.96 |
| 2.1 | 0.194 | 0.160 | 9.53 | 2.31 |

In Table 2 the column headings have the following meanings:

[HA] (μM) concentrates of neutral form of indicator (micromolar)

[A-] (μM) concentrates of anionic form of indicator (micromolar)

$A_{545.9}$ absorbance of organic phase at 545.9 n.m.

$A_{475.5}$ absorbance of organic phase at 475.5 n.m.

These results are also shown in the accompanying Figure which is a graph of indicator concentration (micromolar) against aqueous pH.

An algebraic relationship between the concentration of the indicator species and aqueous pH which gives an experimental constant for the system.

This constant is used to calculate pH in similar two phase systems where the aqueous phase is not accessible.

EXAMPLE 6

Model System Illustrating Application of Indicator as a Method of Calculating Interfacial Area in the Mixing of 2-Phase Systems To a solution of 2,4,5,7-tetrabromofluorescein-n-octyl ester (2.4 millimoles) in 1,1,1-trichloroethane (150 ml) was added solid tetramethyl ammonium bromide ($1.8 \times 10^{-4}$ moles). The resulting suspension was stirred at room temperature until the solid dissolved.

The solution prepared above was added to an equal volume of an aqueous solution of 0.1M tetrasodium pyrophosphate buffered solution whose pH had been adjusted to pH 6 by adding acid.

A 2 phase system was formed which changed colour from yellow-orange to dark red on mixing of the phases. The intensity of the dark-red depended upon the degree of mixing of the phases. On cessation of mixing the 2 phase system re-established itself and the organic phase colour reverted to its original yellow-orange colour.

It should be possible (by using visible reflectance spectroscopy for example) to obtain a correlation between a measurable property of the system and the degree of mixing in the system and hence its interfacial area. This could be used to pre-calibrate solvent extraction equipment where interfacial area is an important variable.

In principle the device works with any salt of tetramethyl ammonium cations—not just the bromide mentioned above.

Any non-miscible organic phase could be used.

Any ester of fluorescein is usable also.

We claim:

1. A process for performing an enzyme-catalysed reaction in a reaction mixture comprising two phases, a first aqueous phase containing an enzyme and a second substantially non-aqueous phase containing a non-water miscible solvent wherein there is present in the non-aqueous phase a compound having the structural formula (I):

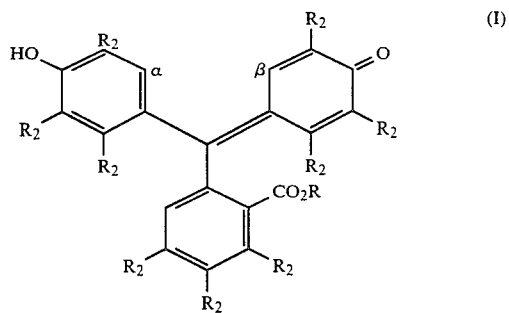

or a compound having the structural formula (II):

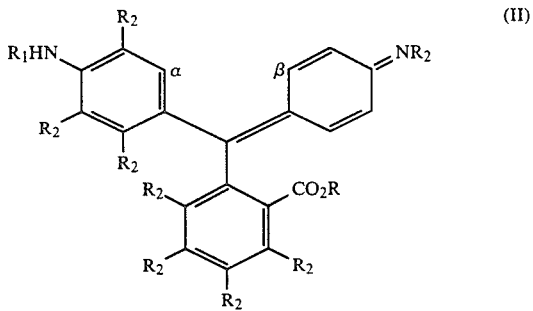

in which positions alpha and beta can be substituted by hydrogen atoms or can be linked together through a bridge comprising 1 or 2 atoms which may have substituents upon them; R is a substituted or unsubstituted hydrocarbon group or a substituted or unsubstituted amide group; $R_1$ is a hydrogen atom, or any other group (the individual groups $R_1$ being the same as or different from each other); and $R_2$ is a hydrogen atom or any other group (individual groups $R_2$ being the same as or different from each other); compound of structural formula (I) or compound of structural formula (II) being present for the purpose of measuring aqueous pH by monitoring spectroscopic properties and calculating the aqueous phase pH therefrom.

2. A process according to claim 1 wherein pH changes are monitored during enzyme-catalysed reactions involving substantially non-aqueous solvent.

3. A process according to claim 1 wherein a non-polar acidic compound is used and a compound having the structural formula (I) is present.

4. A process according to claim 3 wherein an ester is synthesised using a lipase enzyme.

* * * * *